(12) United States Patent
Getsay

(10) Patent No.: US 8,876,789 B1
(45) Date of Patent: Nov. 4, 2014

(54) WITHDRAWAL CATHETER AND METHOD

(76) Inventor: James G. Getsay, Harmony, PA (US)

(*) Notice: Subject to any disclaimer, the term of this patent is extended or adjusted under 35 U.S.C. 154(b) by 587 days.

(21) Appl. No.: 12/924,238

(22) Filed: Sep. 23, 2010

Related U.S. Application Data

(63) Continuation-in-part of application No. 12/378,989, filed on Feb. 23, 2009, now abandoned.

(51) Int. Cl.
*A61M 1/00* (2006.01)
*A61M 5/00* (2006.01)
*A61M 31/00* (2006.01)
*A61M 27/00* (2006.01)
*A61M 25/00* (2006.01)

(52) U.S. Cl.
CPC ............. *A61M 27/00* (2012.01); *A61M 5/00* (2013.01); *A61M 1/00* (2013.01); *A61M 31/00* (2013.01); *A61M 25/00* (2013.01)
USPC ........................... 604/317; 604/540; 604/541

(58) Field of Classification Search
USPC ............ 604/317, 246, 284, 263, 540–543, 48
See application file for complete search history.

(56) References Cited

U.S. PATENT DOCUMENTS

| | | | |
|---|---|---|---|
| 3,771,527 A | | 11/1973 | Ruisi |
| 4,182,343 A | * | 1/1980 | Inaba ........................... 604/268 |
| 4,511,163 A | | 4/1985 | Harris |
| 4,867,747 A | | 9/1989 | Yarger |
| 5,314,406 A | | 5/1994 | Arias |
| 2005/0245887 A1 | | 11/2005 | Olsen |

* cited by examiner

*Primary Examiner* — Tatyana Zalukaeva
*Assistant Examiner* — Benedict L Hanrahan
(74) *Attorney, Agent, or Firm* — Eckert Seamans Cherin & Mellott, LLC; Philip E. Levy

(57) ABSTRACT

A withdrawal catheter and method for removing a material from a specific area includes a first tubing positioned within a second tubing. The first and second tubing has a plurality of holes for withdrawal of the material, such as fluid and small particulates. The first and second tubing may have different wall thicknesses, and the holes may be positioned staggered and have different diameters. At least one of the first and second open ends of the first tubing is connected to a fastener, having a bore for passage of material therethrough. A third tubing is attachable to the fastener for providing a path for the flow of the material from the first and second tubing. The material is aspirated through the first tubing for withdrawing the material. The second tubing substantially prevents larger pieces of material from contacting the first tubing and clogging the holes of the first tubing.

19 Claims, 3 Drawing Sheets

WITHDRAWAL CATHETER AND METHOD

This application is a Continuation-in-Part of U.S. patent application Ser. No. 12/378,989, filed Feb. 23, 2009.

BACKGROUND OF THE INVENTION

The invention relates to the removal of a fluid and other small particles and, more particularly, to an apparatus and method for removing material from a person during a medical procedure.

Various types of equipment are used for withdrawing fluid and other particulates from a person's body during a medical procedure, such as surgery. For example, various types of surgical aspirators, tubing and fittings are used during the treatment of a person.

One example of a treatment that includes the use of an aspirator is chemotherapy. Chemotherapy is the use of chemical substances to treat diseases, such as cancer. To treat a person, chemotherapeutic drugs are infused into a person and used to impair cell division by targeting and damaging fast-dividing cells. Other types of applications may also require the introduction and removal of a fluid or other material.

Often during the use of the aspirator or other medical removal device, the holes of the device become clogged or plugged with pieces of debris, such as tissue, blood clots, or the like. Currently, several types of tip guards, sleeves, or other devices have been used in combination with the aspirator in an attempt to prevent clogging of the holes during fluid removal.

U.S. Pat. No. 4,867,747 to Yarger discloses a surgical aspirator device that can be positioned about a surgical aspirator to aid in preventing clogging of the aspirator holes during use of the aspirator. The surgical aspirator device is a sleeve that can be slid onto the aspirator and has a plurality of orifices. The sleeve also has a plurality of ribs for spacing the aspirator concentrically with respect to the sleeve. However, this sleeve can be only be used with a specific design of aspirator.

Therefore, what is needed is an apparatus and method for withdrawing a fluid and other particulates or debris from a designated area that does not clog during use and that can easily and efficiently remove the material.

SUMMARY OF THE INVENTION

A withdrawal catheter for withdrawing material includes a first tubing having a first end, a second end, and a bore therethrough. The first tubing has a plurality of holes positioned in spaced apart relationship to one another between the first and second ends and positioned in communication with the bore of the first tubing. A second tubing has a first end, a second end, and a bore therethrough. The second tubing has a plurality of holes positioned in spaced apart relationship to one another between the first and second ends and positioned in communication with the bore of the second tubing. The first tubing is disposed within the bore of the second tubing and forming a channel between the first tubing and the second tubing. A connector having at least one connector end is sized for insertion into the bore of the first tubing for attaching the first tubing to the connector.

The plurality of holes may be positioned staggered with respect to one another. The plurality of holes of the first tubing may have a different diameter than the plurality of holes of the second tubing and the wall thickness of the first tubing may have a different thickness than the wall thickness of the second tubing for facilitating withdrawal of the material and reducing clogging of the plurality of holes.

A method of withdrawing a material from a specific area includes the steps of positioning at least one outer tubing about at least one inner tubing, attaching the at least one inner tubing to a piece of equipment for aspirating the material through the at least one inner tubing, positioning a withdrawal catheter having at least one inner tubing and at least one outer tubing in the specific area, substantially preventing clogging of the withdrawal catheter during withdrawal of the material by the positioning of the outer tubing about the inner tubing, and aspirating material through at least one hole in the at least one outer tubing and through at least one hole in the at least one inner tubing for removing the material from the specific area.

BRIEF DESCRIPTION OF THE DRAWINGS

While the specification concludes with claims particularly pointing out and distinctly claiming the subject matter of the invention, it is believed the invention will be better understood from the following description, taken in conjunction with the accompanying drawings, wherein:

DESCRIPTION OF THE PREFERRED EMBODIMENT

The invention described herein provides an apparatus and method for removing a material from a specific area. The apparatus and method can be used in a medical environment, such as during surgery, treatment, or any other procedure, or can be used in any other type of environment or application. The material to be removed may be fluids used during medical procedures, such as chemotherapy drugs, saline solution, or other fluids used during treatment. The material can also include blood or other bodily fluids, small blood clots, small pieces of tissue, such as fat, muscle, or the like, or any other smaller types of material. The apparatus is sized for preventing larger pieces of material from passing through.

The specific area includes regions of a person's body, such as for chemotherapy treatment of cavities, for example, the peritoneal space outside of the stomach or the pleural space outside of the lungs of a person, or for any other desired treatment areas. For areas other than a person's body, the specific area may include any desired area.

Figure 1:
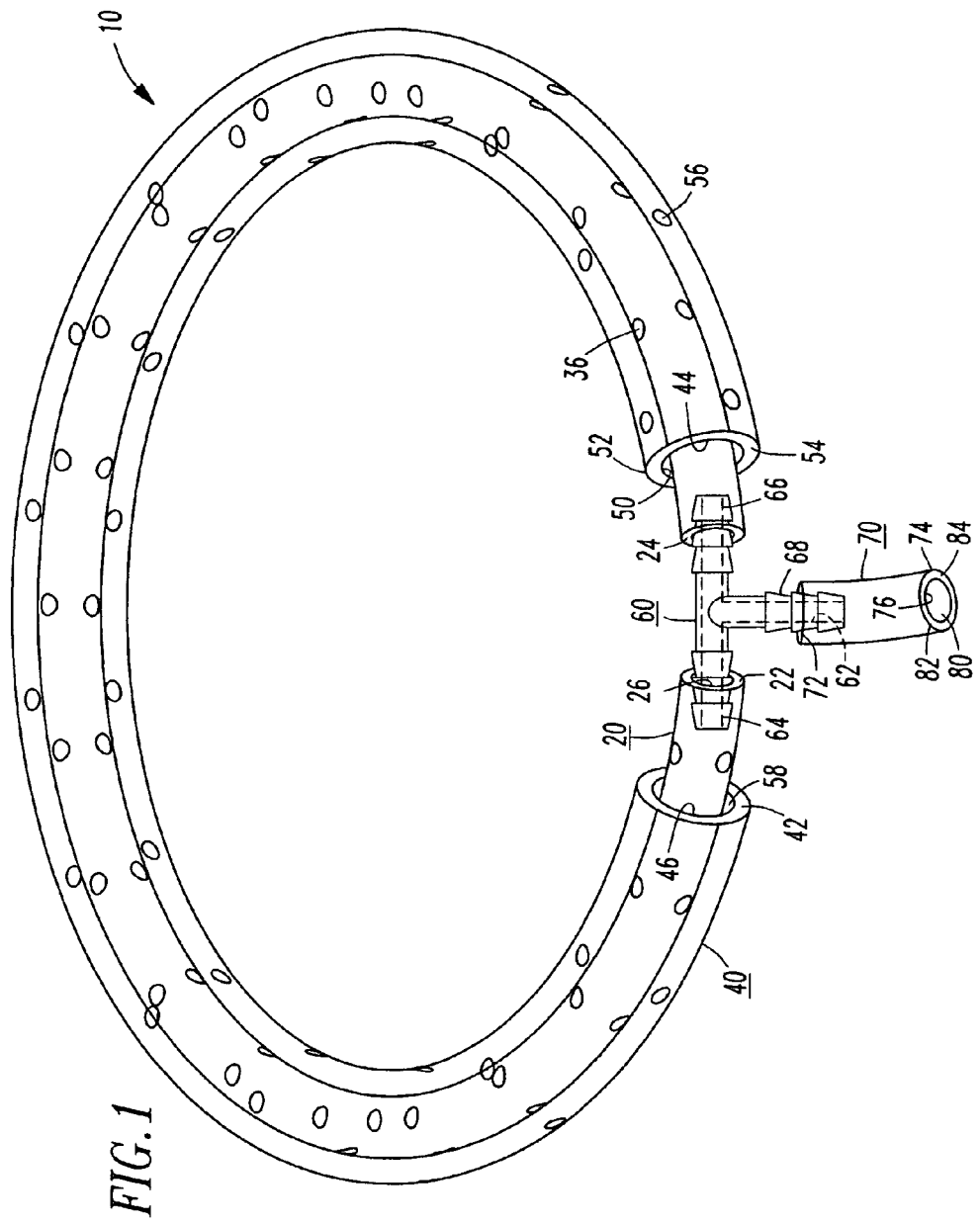
FIG. 1 is a perspective view of a withdrawal catheter.

Referring to FIG. 1, a withdrawal catheter 10 includes a first tubing 20 having a first open end 22, a second open end 24, and a bore 26 extending between the first and second open ends 22 and 24. The first tubing 20 has an inner surface 30 and an outer surface 32 forming a wall 34. The first tubing 20 has at least one hole 36 extending through the wall 34 and intersecting the bore 26. Preferably, the holes 36 are positioned in spaced apart relationship to one another and extend along the length of the first tubing 20.

The withdrawal catheter 10 includes a second tubing 40 having a first open end 42, a second open end 44, and a bore 46 extending between the first and second open ends 42 and 44. The second tubing 40 has an inner surface 50 and an outer surface 52 forming a wall 54. The second tubing 40 has at least one hole 56 extending through the wall 54 and intersecting the bore 46. Preferably, the holes 56 are positioned in spaced apart relationship to one another and extend along the length of the second tubing 40.

The wall 34 of the first tubing 20 and the wall 54 of the second tubing 40 may have the same thickness, or alternatively, may have varying or different thicknesses. Preferably, the outside wall or wall 54 of the second tubing 40 is thicker than the inner wall or wall 34 of the first tubing 20. As one example, the wall thickness of the inner or first tubing 20 may be three quarters the thickness of the wall thickness of the outer or second tubing 40. Having the inner wall 34 thinner makes the first tubing 20 flexible for bending. Also, having the outer wall 54 thicker makes the second tubing 40 rigid enough to maintain the desired shape, while holding the inner tubing 20 round and keeping the first tubing 20 from kinking.

The second tubing 40 may be formed from a single piece of tubing, or alternatively, may include segments of tubing positioned about the first tubing 20. As an example, several pieces of second tubing 40 may be positioned at various locations along the length of the first tubing 40. If tubing segments are used, the second tubing 40 may or may not include the plurality of holes 56.

The first tubing 20 is disposed within the second tubing 40. A channel 58 is formed between the outer surface 32 of the wall 34 of the first tubing 20 and the inner surface 50 of the wall 54 of the second tubing 40. The positioning of the first tubing 20 within the second tubing 40 may be concentric or non-concentric. The channel 58 provides an exit path for the flow of the material. The material to be withdrawn or removed from the specific area can flow through the holes 56 and into the bore 46 of the second tubing 40, through the channel 58, and through the holes 36 of the first tubing 20 and into the bore 36 of the first tubing 20.

Preferably, at least a portion of the holes 36 and the holes 56 are positioned in spaced apart and staggered relationship to one another for providing a plurality of exit points for the material to flow through. If one or several of the holes 36 and 56 become plugged or clogged, there are several other holes 36 and 56 that the material can flow through. The staggered positioning of the holes 36 and 56 substantially prevents clogging of adjacently positioned holes 36 and 56 in the first and second tubing 20 and 40. The holes 36 and 56 are sized for allowing small pieces of material to pass through, while preventing larger pieces of material from passing through. The holes 36 and 56 may be any type of opening, such as a circular or elongated aperture, a slot, a slit, a perforation, orifice, or the like.

The holes 36 and 56 may have the same diameter or may have varying or different diameters with respect to one another. Preferably, the inner or holes 36 of the first tubing 20 are smaller in diameter than the outer or holes 56 of the second tubing 40. The different size of holes facilitates flow of the fluid and reduction of clogging.

The withdrawal catheter 10 includes a fastener with at least one connector end for attachment to the first tubing 20. As one example, the fastener is a connector 60 having a T-shape with a bore 68 therethrough for allowing the material flowing through the first tubing 20 to flow through the bore 68 of the connector 60. Alternatively, the connector 60 may have any suitable shape for facilitating removal of the material.

The connector 60 has a first connector end 64, a second connector end 66, and a third connector end 68. The first and second connector ends 64 and 66 are attachable to the first and second open ends 22 and 24 of the first tubing 20 for securing the first tubing 20 to the connector 60. The attachment of the first tubing 20 to the first and second connectors 64 and 66 of the connector 60 positions the tubing 20 into a substantially circular, oblong, elliptical or the like type of shape and provides a continuous loop for the flow of the material through the bore 26 and the bore 62.

A third tubing 70 is attachable to the third connector end 68 of the connector 60 for discharging the material flowing through the connector 60. The third tubing 70 provides an outlet for the flow of material from the first and second tubing 20 and 40. The third tubing 70 has a first open end 72, a second open end 74, and a bore 76 extending between the first and second open ends 72 and 74. The third tubing 70 has an inner surface 80 and an outer surface 82 forming a wall 84. Since the bore 26 of the first tubing 20 and the bore 62 of the connector 60 are positioned in fluid communication with the bore 76 of the third tubing 70, the material is able to flow from the first tubing 20, through the bore 76 of the third tubing 70, and out of the withdrawal catheter 10.

For the various embodiments of this invention, the same reference characters will be used to designate like parts. In addition, like functions and like interactions of the parts among the various embodiments of this invention will not be repeated for each embodiment.

Figure 2:
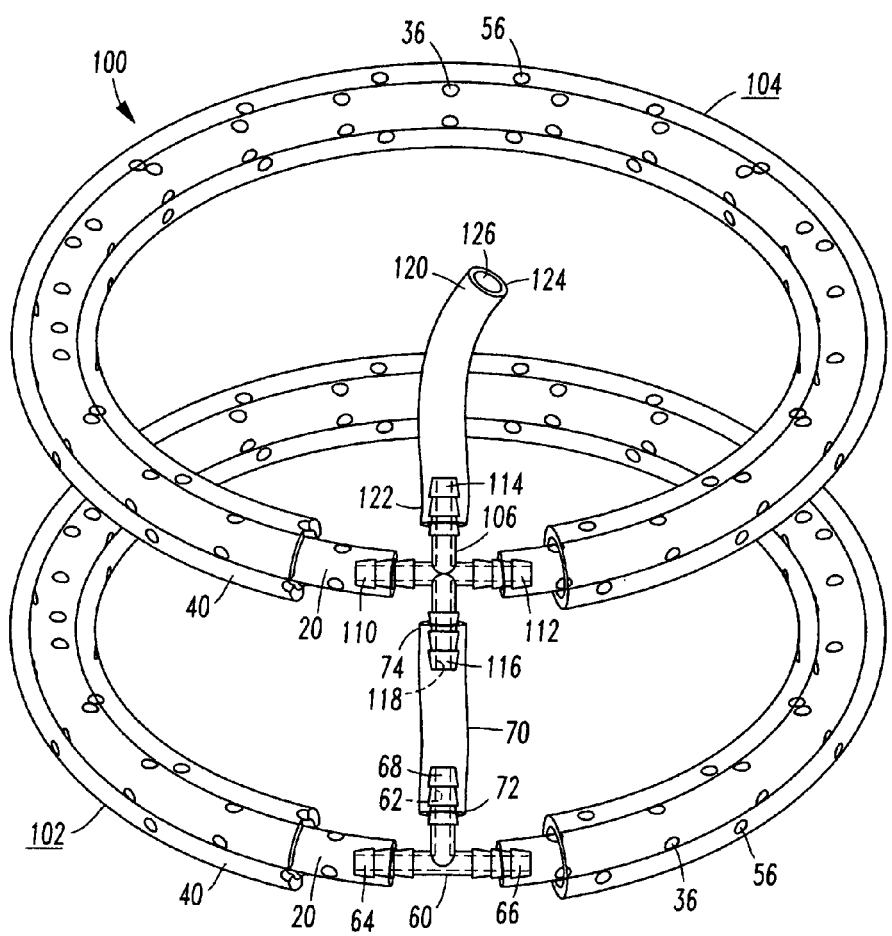
FIG. 2 is an alternative view of the withdrawal catheter having a first set and a second set of tubing.

Referring to FIG. 2 and using the same reference characters to define like parts, an alternative embodiment of the withdrawal catheter 10 as illustrated in FIG. 1 may be a withdrawal catheter 100 having a first set 102 of the first and second tubing and a second set 104 of the first and second tubing connected together. The first set 102 includes the first tubing 20 disposed within the second tubing 40, and having the first tubing 20 attached to the connector 62. The second set 104 includes the first tubing 20 disposed within the second tubing 40, and having the first tubing 20 attached to a second fastener, such as a connector 106. The connector 106 is a cross-shaped fastener having a first connector end 110, a second connector end 112, a third connector end 114, a fourth connector end 116, and a bore 118 therethrough. The bore 118 is positioned in fluid communication with the bore 26 of the first tubing 20 for the removal of the material. Alternatively, the connector 106 may be any suitable shape for facilitating removal of the material.

The first open end 72 of the third tubing 70 is attached to the third connector end 68 of the connector 62 and the second open end 74 of the third tubing 70 is attached to the fourth connector end 116 of the connector 106.

A fourth tubing 120 has a first open end 122 and a second open end 124 with a bore 126 extending therebetweeen. The first open end 122 of the fourth tubing 120 is attached to the third connector end 114 of the connector 106. The second open end 124 of the fourth tubing 120 extends outwardly from the second set 104 for attachment or engagement with another piece of equipment, such as a suctioning device or other device. The use of the two sets of first and second tubing 20 and 40 provides for a larger volume of material being removed simultaneously and access to a greater area.

Figure 3:
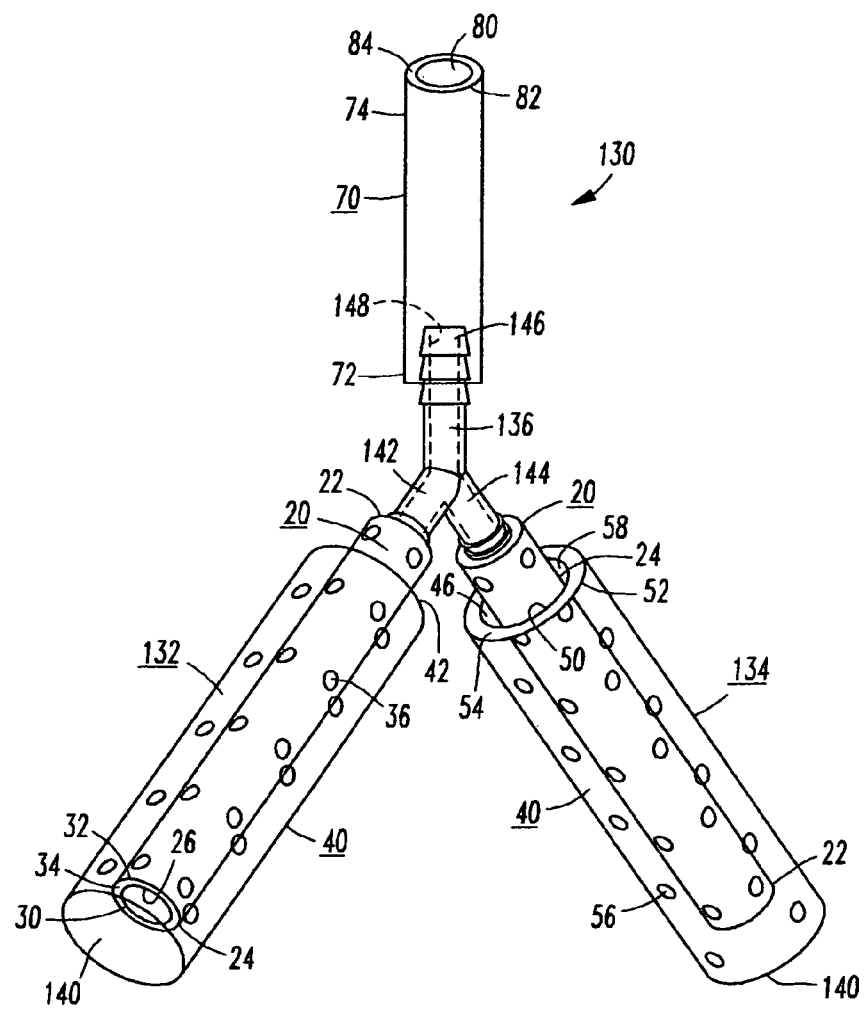
FIG. 3 is another alternative view of the withdrawal catheter having a y-shape.

Referring to FIG. 3 and using the same reference characters to define like parts, an alternative embodiment of the withdrawal catheter 10 as illustrated in FIG. 1 may be a withdrawal catheter having at least one first tubing 20 and at least one second tubing 40 with only one end of the first tubing 20 attached to a connector, and the opposite end of the first tubing 20 extending outwardly and unattached to the connector. The first tubing 20 may have a snake-like shape, a curved shape, a straight shape, or any other suitable shape. The second tubing has a shape corresponding to the type of shape of the first tubing for enabling the first tubing to be disposed within the second tubing. The first and second tubing 20 and 40 may be flexible, rigid or combinations thereof.

As an example, referring to FIG. 3, a withdrawal catheter 130 has a first set 132 of the first and second tubing and a second set 134 of the first and second tubing connected together. The first set 132 includes the first tubing 20 disposed within the second tubing 40, and having only one of the open ends, such as first open end 22, of the first tubing 20 attached to a connector 136. The other of the open ends, such as second open end 24, of the first tubing 20 is unattached and extends outwardly from the connector 136. The second set 134 includes the first tubing 20 disposed within the second tubing 40, and also having only one of the open ends 22 or 24 of the first tubing 20 attached to the connector 136. The other of the open ends 22 or 24 of the first tubing 20 is unattached and extends outwardly from the connector 136.

The second tubing 40 has one open end, such as first open end 42 and one closed end 140. The closed end 140 prevents the entry of material into the second tubing 40 through the end 140. The closed end 140 may be integrally formed with the second tubing 40 or may be a separate piece, such as a cap or the like, attached to the end 140. The closed end 140 may be flat, arched concave or convex, have radiused edges, or have any other suitable shape.

The connector 136 includes a first connector end 142, a second connector end 144, a third connector end 146, and a bore 148 therethrough. The bore 148 is positioned in fluid communication with the bore 26 of the first tubing 20 for the removal of the material. Preferably, the connector 136 is Y-shaped, but alternatively, may have any suitable shape for facilitating removal of the material.

The first and second connector ends 142 and 144 are attachable to either of the first and second open ends 22 or 24 of first inner tubing 20. The other of the first and second open ends 22 or 24 of the inner tubing 20 is positioned at the closed end 140 of the second outer tubing 40.

One of the open ends 72 or 74 of the third tubing 70 is attachable to the third connector end 146 of the connector 136. The other of the open ends 72 or 74 is attachable to another piece of equipment. The design of the Y-shaped withdrawal catheter 130 enables the catheter 130 to be positioned in various locations and at different orientations for facilitating withdrawal of the material.

In operation, the withdrawal catheter 10, 100, or 130 is positioned in a desired location, such as an interperitoneal cavity of a person. The inner first tubing 20 is attachable to a suction device or other piece of equipment. The outer second tubing 40 can be maintained in position by the friction existing between the first and second tubing 20 and 40.

When suction or any other type of withdrawing force, such as gravity, a siphon, or the like, is applied to the first tubing 20, material, such as fluid, small particulates, blood, fat, or other pieces of material, is aspirated from the specific area through the holes 56 of the second tubing 40, through the bore 46 of the second tubing 40, through at least a portion of the channel 60, through the holes 36 of the first tubing 20, and through the bore 26 of the first tubing 20. Aspirate is the withdrawal of the material from the specific area. During aspiration, the material moves away from the specific area and toward the pump or other piece of equipment withdrawing the material from the specific area.

For the withdrawal catheter 10, the material is then withdrawn through the connector 60 and through the third tubing 70. Using the withdrawal catheter 100, the material is withdrawn through both the first set 102 of tubing, through the bore 62 of the connector 60, through the third tubing 70, and through the second set 104 of tubing. The material is then withdrawn through the connector 106 and through the fourth tubing 120. For the withdrawal catheter 130, the material is withdrawn through the first and second sets 132 and 134 of tubing, and then through the connector 136 and through the third tubing 70.

An advantage of the withdrawal catheter 10, 100 and 130 is that the use of double tubing, such as first and second tubing 20 and 40, reduces the amount of clogging or plugging of the holes 36 and 56. Larger pieces of material may contact and clog a few of the holes 56 of the outer second tubing 40, but will be prevented from entering the holes 56 of the outer second tubing 40. Since the larger pieces of material will remain on the outer surface 52 of the second tubing 40, the larger pieces of material will not come into contact with the inner first tubing 20. This design substantially prevents the holes 36 of the inner first tubing 20 from becoming clogged or plugged with the larger pieces of material.

Another advantage of the double tubing is that the suction or other withdrawal procedure can be applied to only the inner or first tubing 20. The outer or second tubing 40 can be used as a shield to the inner tubing 20.

Another advantage of the withdrawal catheter 10, 100 and 130 is that the plurality of holes 36 and 56 substantially reduces the amount of clogging and plugging of the holes by small and large pieces of material. In the event that some of the holes 35 and 56 become clogged, there are a sufficient number of other holes 36 and 56 that the material may flow through the unclogged holes 36 and 56.

Yet another advantage is that the holes 36 and 56 are sized and positioned for allowing fluid and smaller pieces of material through, but at the same time preventing the flow of larger pieces of material through. Also, the holes 36 and 56 may have different diameters for preventing clogging.

Another advantage is that the holes 36 and 56 are positioned staggered with respect to one another for preventing clogging and facilitating flow of the material through the holes 36 and 56.

Yet another advantage is that the wall thickness of the first tubing 20 and the second tubing 40 may be different enabling the shape of the withdrawal catheter to be flexible for varied positioning of the first and second tubing 20 and 40.

Thus there has been shown and described a novel apparatus and method for removing material which fulfills all the objects and advantages sought therefor. Many changes, modifications, variations and other uses and applications of the subject invention will, however, become apparent to those skilled in the art after considering this specification together with the accompanying drawings and claims. All such changes, modifications, variations and other uses and applications which do not depart from the spirit and scope of the invention are deemed to be covered by the invention which is limited only by the claims which follow.

I claim:

1. A withdrawal catheter for withdrawing material, comprising:
    at least one first tubing having a first end, a second end, and a bore therethrough, the at least one first tubing having a plurality of holes positioned in spaced apart relationship to one another between the first and second ends and positioned in communication with the bore of the at least one first tubing, the at least one first tubing having a first wall extending from the first end to the second end, the first wall having an inner surface and an outer surface defining an outer diameter of the at least one first tubing, the first wall having a substantially uniform thickness circumferentially extending from the first end to the second end;
    at least one second tubing having a first end, a second end, and a bore therethrough, the at least one second tubing having a plurality of holes positioned in spaced apart relationship to one another between the first and second ends of the at least one second tubing and positioned in communication with the bore of the at least one second tubing, the at least one second tubing having a second wall extending from the first end to the second end, the second wall having an outer surface and an inner surface defining an innermost diameter of the at least one second tubing, the at least one first tubing disposed within the bore of the at least one second tubing and forming a channel between the at least one first tubing and the at least one second tubing, the innermost diameter of the at least one second tubing being greater than the outer diameter of the at least one first tubing such that the positioning of the at least one first tubing relative to the at least one second tubing may be concentric or non-concentric wherein there may be intermittent contact between the outer surface of the at least one first tubing and the inner surface of the at least one second tubing along a length of the at least one second tubing, the second wall having a substantially uniform thickness circumferentially extending from the first end to the second end;

the plurality of holes of the at least one first tubing and the plurality of holes of the at least one second tubing positioned in communication with one another, in communication with the bores of both of the at least one first and second tubing, and in communication with the channel for enabling the material to be withdrawn through at least one of the plurality of holes of the at least one second tubing, through at least a portion of the channel, through at least one of the plurality of holes of the at least one first tubing, and through at least a portion of the bores of the at least one first and second tubing;

at least a portion of the plurality of holes of the at least one first tubing and the at least one second tubing positioned staggered and unaligned with one another; and at least one connector having at least one connector end and a bore therethrough, the at least one connector end sized for coupling to the bore of the at least one first tubing for attaching the at least one first tubing to the at least one connector for withdrawing the material out of the at least one first tubing, out of the bore of the at least one connector, and out of the withdrawal catheter.

2. The withdrawal catheter according to claim 1, wherein the first end of the at least one first tubing is attached to the at least one connector and the second end of the at least one first tubing is attached to the at least one connector for forming a continuous loop for the material to flow through.

3. The withdrawal catheter according to claim 1, further comprising a third tubing having a bore therethrough and attachable to the at least one connector for withdrawing the material from a desired area.

4. The withdrawal catheter according to claim 1, wherein at least a portion of the plurality of holes of the least one first tubing have a different diameter than at least a portion of the plurality of holes of the at least one second tubing.

5. The withdrawal catheter according to claim 1, further comprising the plurality of holes of the at least one first tubing having a diameter smaller than a diameter of the plurality of holes of the at least one second tubing for facilitating withdrawal of the material.

6. The withdrawal catheter according to claim 1, further comprising:
a first set having one of the at least one first tubing and one of the at least one second tubing;
a second set having another of the at least one first tubing and another of the at least one second tubing; and
the at least one connector having a first connector end, a second connector end, and a third connector end forming a y-shaped connector, one of the at least one first tubing of the first set attached to the first connector end, one of the at least one first tubing of the second set attached to the second connector end for withdrawing the material from multiple areas simultaneously.

7. The withdrawal catheter according to claim 1, further comprising the at least one first tubing having a thinner wall thickness than a wall thickness of the at least one second tubing, the thinner wall thickness providing flexibility to the at least one first tubing for preventing kinking in the at least one first tubing and the wall thickness of the at least one second tubing providing rigidity to the at least one second tubing for supporting the at least one first tubing within the bore of the at least one second tubing.

8. The withdrawal catheter according to claim 1, further comprising the at least one first tubing having a wall thickness that is approximately three-quarters of a wall thickness of the at least one second tubing.

9. The withdrawal catheter according to claim 1, further comprising:
the at least one second tubing having at least one of the first and second ends open and the other of the first and second ends closed; and
at least one of the first and second ends of the at least one first tubing connected to the at least one connector and the other of the first and second ends of the at least one first tubing unattached and extending toward the closed end of the at least one second tubing.

10. The withdrawal catheter according to claim 1, wherein the at least one second tubing includes several segments of tubing disposed about the at least one first tubing.

11. A withdrawal catheter for withdrawing a material from a specific area, comprising:
at least one first tubing having a first open end and a second open end, the at least one first tubing having a first wall extending between the first open end and the second open end and having a plurality of holes positioned therethrough, the first wall having an inner surface and an outer surface defining an outer diameter of the at least one first tubing, the first wall having a substantially uniform thickness circumferentially extending from the first open end to the second open end;
at least one second tubing having a first open end and a second end, the at least one second tubing having a second wall extending between the first open end and the second end and having a plurality of holes positioned therethrough, the second wall having an outer surface and an inner surface defining an innermost diameter of the at least one second tubing, the second wall having a substantially uniform thickness circumferentially extending from the first open end to the second end, the at least one second tubing positioned about the at least one first tubing for forming a channel therebetween, the innermost diameter of the at least one second tubing being greater than the outer diameter of the at least one first tubing such that the positioning of the at least one first tubing relative to the at least one second tubing may be concentric or non-concentric wherein there may be intermittent contact between the outer surface of the at least one first tubing and the inner surface of the at least one second tubing along a length of the at least one second tubing;
at least one fastener having a bore therethrough, the at least one fastener secured to at least one of the first and second open ends of the at least one first tubing, and the bore of the at least one fastener positioned in fluid communication with the at least one first tubing;

the plurality of holes of the at least one first tubing positioned in communication with the plurality of holes of the at least one second tubing, the plurality of holes of the at least one first and second tubing positioned in communication with the channel and positioned in communication with the bore of the fastener;

the first wall of the at least one first tubing having a thinner wall thickness with a different thickness as compared to a wall thickness of the second wall of the at least one second tubing for enabling the at least one first tubing to be flexible and the at least one second tubing to be rigid enough to keep the at least one first tubing from kinking; and the material flowing through at least one of the plurality of holes of the at least one first tubing and the at least one second tubing, through at least a portion of the channel, and through the bore of the at least one fastener for withdrawing the material from the specific area.

12. The withdrawal catheter according to claim 11, wherein the first end of the at least one first tubing is attached to the at least one fastener and the second end of the at least one first tubing is attached to the at least one fastener for forming a continuous loop for the material to flow through.

13. The withdrawal catheter according to claim 11, further comprising at least a portion of the plurality of holes of the at least one first and second tubing positioned staggered and unaligned with respect to one another.

14. The withdrawal catheter according to claim 11, further comprising at least a portion of the plurality of holes of the at least one first tubing having a diameter that is different than a diameter of the plurality of holes of the at least one second tubing.

15. The withdrawal catheter according to claim 11, further comprising at least a portion of the plurality of holes of the at least one first tubing having a diameter that is smaller than a diameter of the plurality of holes of the at least one second tubing for facilitating withdrawal of the material.

16. The withdrawal catheter according to claim 11, further comprising;
   a first set having one of the at least one first tubing and one of the at least one second tubing;
   a second set having another of the at least one first tubing and another of the at least one second tubing; and
   the at least one connector having a first connector end, a second connector end, and a third connector end forming a y-shaped connector, one of the at least one first tubing of the first set attached to the first connector end, one of the at least one first tubing of the second set attached to the second connector end for withdrawing the material from multiple areas simultaneously.

17. The withdrawal catheter according to claim 11, further comprising the at least one first tubing having a wall thickness that is approximately three-quarters the thickness of a wall thickness of the at least one second tubing.

18. The withdrawal catheter according to claim 11, further comprising a third tubing attachable to the at least one fastener for withdrawing material from the desired area.

19. The withdrawal catheter according to claim 11, further comprising:
   the at least one second tubing having at least one of the first and second ends open and the other of the first and second ends closed; and
   at least one of the first and second ends of the at least one first tubing connected to the at least one fastener and the other of the first and second ends of the at least one first tubing unattached and extending toward the closed end of the at least one second tubing.

\* \* \* \* \*

UNITED STATES PATENT AND TRADEMARK OFFICE
CERTIFICATE OF CORRECTION

| | | |
|---|---|---|
| PATENT NO. | : 8,876,789 B1 | Page 1 of 1 |
| APPLICATION NO. | : 12/924238 | |
| DATED | : November 4, 2014 | |
| INVENTOR(S) | : James G. Getsay | |

It is certified that error appears in the above-identified patent and that said Letters Patent is hereby corrected as shown below:

In the Specification

Column 6, line 21, "35" should read --36--.

Signed and Sealed this
Eighteenth Day of August, 2015

Michelle K. Lee
*Director of the United States Patent and Trademark Office*